United States Patent [19]

Peterson et al.

[11] Patent Number: 5,220,825

[45] Date of Patent: Jun. 22, 1993

[54] APPARATUS FOR COLLECTING PARTICULATE SAMPLES

[75] Inventors: Michael L. Peterson; Peter J. Hernes; David Thoreson; John I. Hedges, all of Seattle, Wash.

[73] Assignee: Board of Regents of the University of Washington, Seattle, Wash.

[21] Appl. No.: 782,240

[22] Filed: Oct. 23, 1991

[51] Int. Cl.$^5$ .............................................. G01N 1/20
[52] U.S. Cl. ................................. 73/863.01; 222/368; 210/534
[58] Field of Search ...................... 43/58, 60; 73/61.4, 73/170 R; 222/363, 368; 210/533, 534

[56] References Cited

U.S. PATENT DOCUMENTS

| | | | |
|---|---|---|---|
| 1,904,062 | 4/1933 | Laughlin et al. | 210/534 |
| 1,996,044 | 3/1935 | Green | 222/363 X |
| 2,411,220 | 11/1946 | McDargh, Jr. | 222/363 |
| 4,321,823 | 3/1982 | Anderson | 73/61.4 |
| 4,383,545 | 5/1983 | Becker | 222/368 X |

OTHER PUBLICATIONS

Letter to Dr. Neil Anderson from John Hedges dated Jul. 18, 1989.
Progress Report entitled "The Effectiveness of Poisons and Preservatives on the Composition of Organic Matter Collected in Sediment Traps," prepared by John Hedges amd dated Jul. 18, 1989.
Regulations of the National Science Foundation Regarding Information Dissemination to the Public, pp. II-5, VII-4 and VII-5.

Primary Examiner—John C. Fox
Attorney, Agent, or Firm—Stoel Rives Boley Jones & Grey

[57] ABSTRACT

Multi-chamber devices of collecting particles in aquatic environments including an upper chamber serving as a particle interceptor chamber, a lower chamber serving as a particle accumulator chamber, and a valve assembly interposed between the upper and lower chambers are disclosed. Upon rotation of an indented valve body, particles in the upper chamber are transferred to the lower chamber and preserved for analysis. The valve assembly substantially reduces the presence of living organisms in particle samples and enhances the accuracy of passive vertical particle flux sampling techniques. A plurality of sample collection chambers may be provided to facilitate temporal resolution of vertical particle flux measurements during a single deployment period.

26 Claims, 4 Drawing Sheets

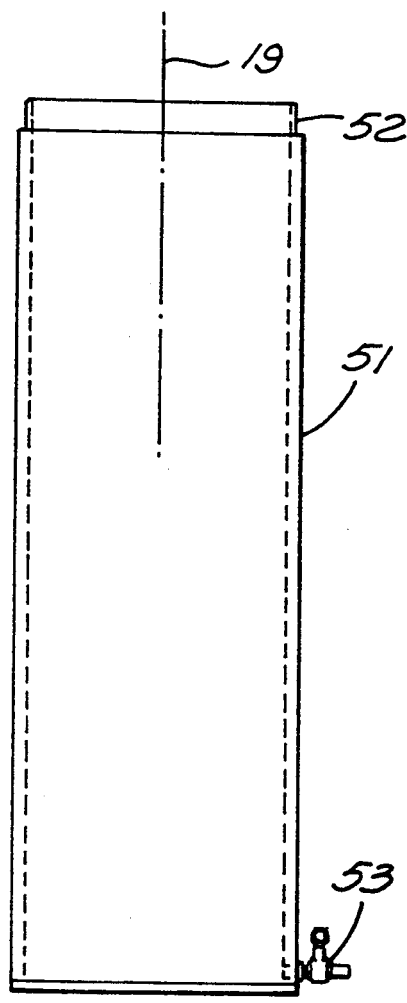
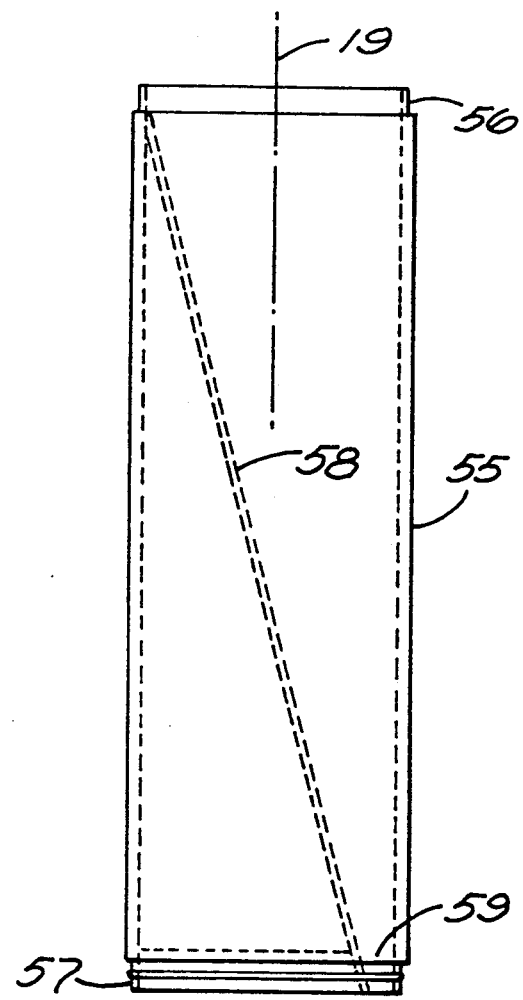
FIG. 8
FIG. 9
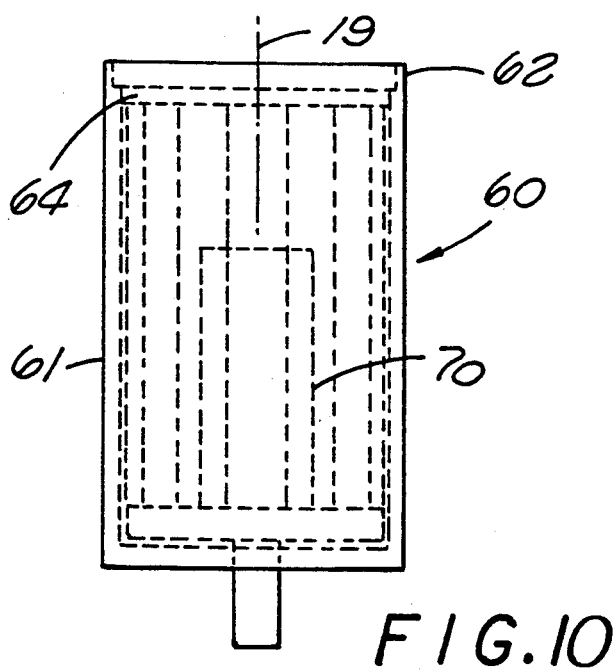
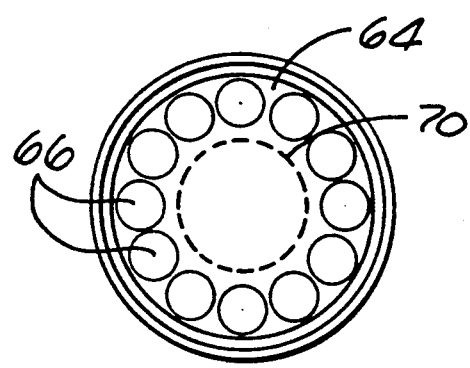
FIG. 10
FIG. 10A

APPARATUS FOR COLLECTING PARTICULATE SAMPLES

This invention was made with U.S. government support under Grant Nos. OCE-8711016 and OCE-9015914 awarded by the National Science Foundation. The U.S. Government has certain rights in this invention.

TECHNICAL FIELD

This invention relates to an apparatus for collecting and selectively transferring particulate material. A preferred embodiment relates more specifically to a sediment trap for collecting samples of passively sinking particles in marine and lacustrine environments.

BACKGROUND OF THE INVENTION

Scientists have recognized that there is a significant particle flux from the surface waters of aquatic environments such as oceans and lakes to the deeper zones and underlying sediments. This phenomenon is conventionally referred to as the vertical particle flux. Quantitative measurement, as well as analysis of the composition of the vertical particle flux, is of significant interest to scientists. Vertical particle flux data provides insights into many important aquatic processes, including the rate and magnitude of downward transport of particulate materials, seasonality of downward fluxes, coupling between vertically stratified ecosystems, and water column regeneration rates. Conventional, pre-sediment trap water sampling techniques could not quantify, and generally did not even detect the vertical particle flux phenomenon. It was not until sediment traps were placed at various depths in the water column that this "rain" of sinking particles became evident.

Sediment traps have been used widely in recent years in an attempt to quantify aquatic particle fluxes. Early sediment traps were essentially containers, such as cans, placed open end up in an aqueous environment to collect particles sinking through the water column. Hydrodynamic disturbances in the open-ended containers caused loss of the collected particulate material from the trap during retrieval of the trap, as well as washout of particulate material from the trap during collection. These sample losses resulted in significant inaccuracies in particle flux measurements. The size and frequency of hydrodynamic disturbances, e.g., eddy formation, and the liquid flow pattern within and around a trap varies substantially depending upon trap geometry, particle type and the local current regime.

In general, it is primarily the passively sinking (inanimate) particle flux that is of interest in vertical flux studies. The organic components of this particle flux are labile toward microbial degradation, requiring that sediment traps used for collection periods of any significant duration (e.g., 2315 in excess of one day) be treated with biocides to prevent decomposition of the collected sample. In open traps, zooplankton and other living aquatic organisms, referred to as "swimmers", enter the sediment collection chamber and distort the vertical particle flux measurements. In some aquatic environments, the portion of the vertical particle flux measurement attributable to swimmers may significantly exceed that portion attributable to passively sinking, inanimate particles. Additionally, "grazing" by swimmers on collected particulate material further distorts passive vertical particle composition and flux measurements. Considerable attention has been devoted to the identification of swimmers in and their removal from sediment samples, as well as accounting for inaccuracies resulting from the presence of swimmers in sediment samples.

Another inadequacy with respect to conventional sediment traps is that a trap having a single collection chamber cannot provide temporal resolution of the vertical particle flux. To quantify the vertical particle flux over time, several traps may be separately deployed and retrieved at various time intervals. This process is time consuming and labor intensive, and therefore highly impractical, particularly in aquatic environments that are inaccessible by virtue of their distance from inhabited regions.

Many attempts have been made to provide sediment collection traps that accurately reflect natural vertical particle fluxes. Loss of collected particulate material resulting from hydrodynamic disturbances has been addressed by placement of baffles at various locations within traps, or utilization of lid mechanisms that allow trap deployment and retrieval in a closed configuration. Sediment trap configurations have included narrow-mouthed, jar-like containers, as well as wide-mouthed funnels having narrower sample chambers. These sediment trap design innovations have been somewhat successful in reducing particle loss due to hydrodynamic disturbances, particularly during retrieval of the traps.

Exclusion of swimmers from the particle collection zone of sediment traps and preservation of the particulate material during collection pose difficult challenges. The dissolved poison or preservative must be isolated from other areas of the trap to prevent the killing of swimmers and consequent distortion of the collected sample composition. Relatively dense brines are typically used to isolate poisons and preservatives in a sediment collection zone, and to retain dissolved or leached sample components in the collection zone. Sediment traps having fine screens positioned within the traps above the collection zone to exclude living organisms from the collection area have been devised. Alternatively, labyrinth-type sediment traps have been developed that utilize a series of funnels to direct passively sinking particles to a collection chamber, while allowing mobile zooplankton to "escape" into a secondary poisoned chamber.

Despite these efforts, the recent U.S. Global Ocean Flux Study Workshop on Sediment Trap Technology and Sampling sponsored by the National Science Foundation concluded that current sediment trap technology is inadequate to exclude living organisms, and that a high priority should be given to eliminating swimmers from sediment trap collections. There was considerable discussion during the workshop regarding the need for more accurate collection techniques and preservation of the composition of collected samples. Additionally, the workshop report noted that hydrodynamic biases must continue to be monitored. U.S. Global Ocean Flux Study, "Sediment Trap Technology and Sampling", Report of the U.S. GOFS Working Group on Sediment Trap Technology and Sampling, published August 1989.

The incentive to design an improved sediment trap came out of recent field studies on the performance of conventional (open) sediment traps that were carried out in cooperation with colleagues Dr. Cindy Lee (Marine Sciences Research Center, State University of New York) and Dr. Stuart Wakeham (Skidaway Institute of Oceanography). The main purpose of the research project was to investigate the ability of commonly used poisons and preservatives to prevent alteration and decomposition of different types of organic matter collected in sediment traps. This was accomplished both by laboratory studies (Lee et al., in press) and by deploying sediment traps treated with different combinations of poisons and preservatives in a local marine embayment, Dabob Bay, and determining the organic compositions and fluxes after collection periods ranging from weeks to months. Although several effective biocides were identified in the field and laboratory (Lee et al., in press), it became clear that conventional (unvalved) sediment traps were nevertheless subject to a variety of washout, reprocessing, and swimmer problems that could only be addressed by an improved physical design (Lee et al., in press; Wakeham et al, in preparation; Hedges et al, in preparation). This effort would not have been initiated without the clear demonstration of artifacts intrinsic to open sediment traps that resulted from the project with Drs. Lee and Wakeham.

Accordingly, it would be advantageous to develop a sediment trap for collecting vertical particle flux samples in aquatic environments that includes one or more of the following features: provides isolation of the collected sediment sample from washout by ambient water currents; prevents live organisms from entering the collection chamber of the trap and reduces sample distortion resulting from grazing by swimmers; reduces measurement biases introduced as a result of hydrodynamic effects; allows temporal resolution of vertical particle flux measurements by providing collection of a plurality of sediment samples during a single deployment period; preserves dissolved as well as solid species within the collection chamber; provides a flexible, modular design and programmable monitoring and control functions; and is capable of operating as a self-contained assembly at depths of up to several thousand meters.

SUMMARY OF THE INVENTION

Sediment traps of the present invention comprise multi-chamber collection devices having an upper chamber serving as a particle interceptor chamber and a lower unit serving as a particle accumulator and/or collection chamber, with a valve assembly including tightly sealed indented valve body interposed between the chambers. Upon periodic rotation of the indented valve body, passively sinking particles collected at the bottom of the upper particle interceptor chamber are selectively transferred to the lower accumulator and/or collection unit. Freely swimming organisms are unlikely to reside within the indentations of the valve body during the rotation period, and thus are effectively excluded when passively sinking particles are transferred to the lower unit. The sediment trap additionally includes sealing means for isolating the lower particle accumulator unit from the upper particle interceptor chamber, except during rotation of the valve body. The sediment trap of the present invention substantially reduces washout and the transfer of swimmers from the sediment interceptor chamber to the accumulator and thereby enhances the accuracy of passive vertical particle flux sampling techniques.

Sediment traps of the present invention preferably include a plurality of sample collection chambers, permitting collection of a plurality of samples over continuous or intermittent time intervals. This may be accomplished by utilizing a carousel-like rotating sediment collection assembly having a plurality of discrete collection vials, whereby sediment transferred to the sediment accumulator chamber during predetermined time intervals is directed to discrete collection vials. This feature provides temporal resolution of vertical particle flux measurements during a single deployment period.

According to preferred embodiments, sediment traps of the present invention are constructed to provide modular assembly of components. Modular construction facilitates replacement and/or interchangeability of particle interceptor chambers, valve assemblies, particle accumulator units, and sample collection assemblies. Selected trap components may also be adapted for use and interchanged with other types of traps and trap components.

Operation of the valve assembly and/or sediment collection assembly may be automated and controlled by means of motors electrically connected to a programmable microprocessor unit. The microprocessor unit preferably provides programmable monitoring and control functions that lend even greater versatility to the traps and increase the amount and accuracy of information gathered during any deployment period. The microprocessor unit may also provide interactive yet independent control of a plurality of sediment traps. Enhancement features such as remote visual monitoring by underwater monitoring means may also be incorporated.

The valve assembly of the present invention may additionally be adapted for use in a variety of applications to selectively transfer particles, liquids or objects from locations above the surface of the valve body to locations below the surface of the valve body. It may be used, for example, in subaerial particulate sample collecting devices or other than natural aquatic environments, or in metering, automatic sizing, or automatic positioning applications. Although preferred embodiments utilize a spherical valve body, different configurations and specialized indentation patterns provide a variety of sizing and metering functions.

BRIEF DESCRIPTION OF THE DRAWINGS

The above-mentioned and additional features of the present invention and the manner of obtaining them will become apparent, and the invention will be best understood by reference to the following more detailed description, read in conjunction with the accompanying drawings, in which:

FIG. 8 shows a side view of a particle accumulator chamber suitable for use as a collection chamber;

FIG. 9 shows a side view of a particle accumulator chamber incorporating a skewed focusing funnel for directing particulate material to a lower collection chamber; and FIG. 10 shows a side view of a sediment collection assembly in the form of a carousel; and FIG. 10A shows a top view of the carousel of FIG. 10 illustrating a plurality of sample collection positions.

DETAILED DESCRIPTION OF PREFERRED EMBODIMENTS

Figure 1:
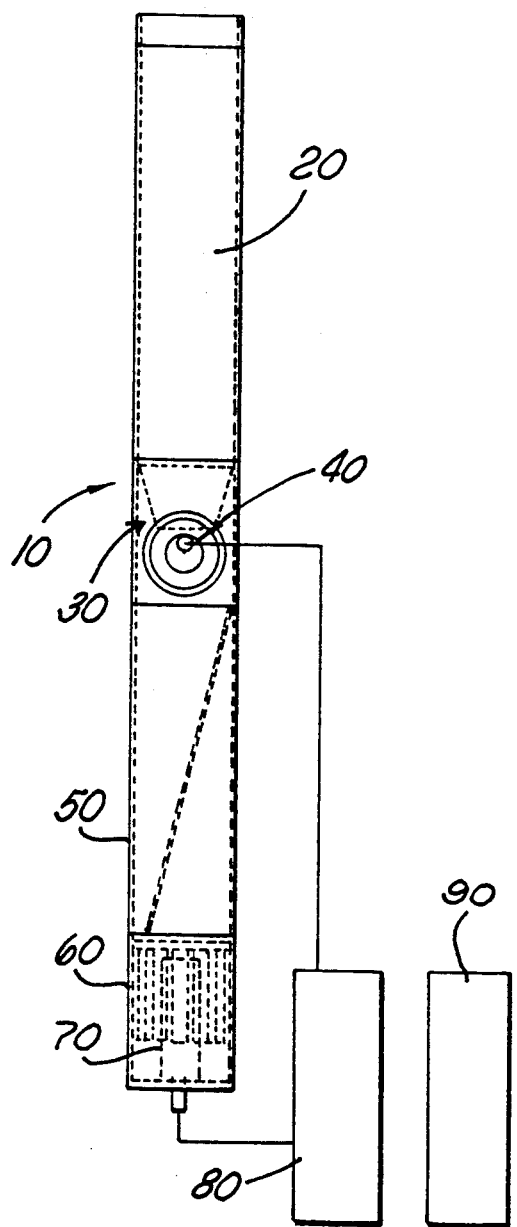
FIG. 1 is a schematic representation of a multiple sample, modular cylindrical sediment trap of the present invention controllable by a microprocessor unit.
Figure 2:
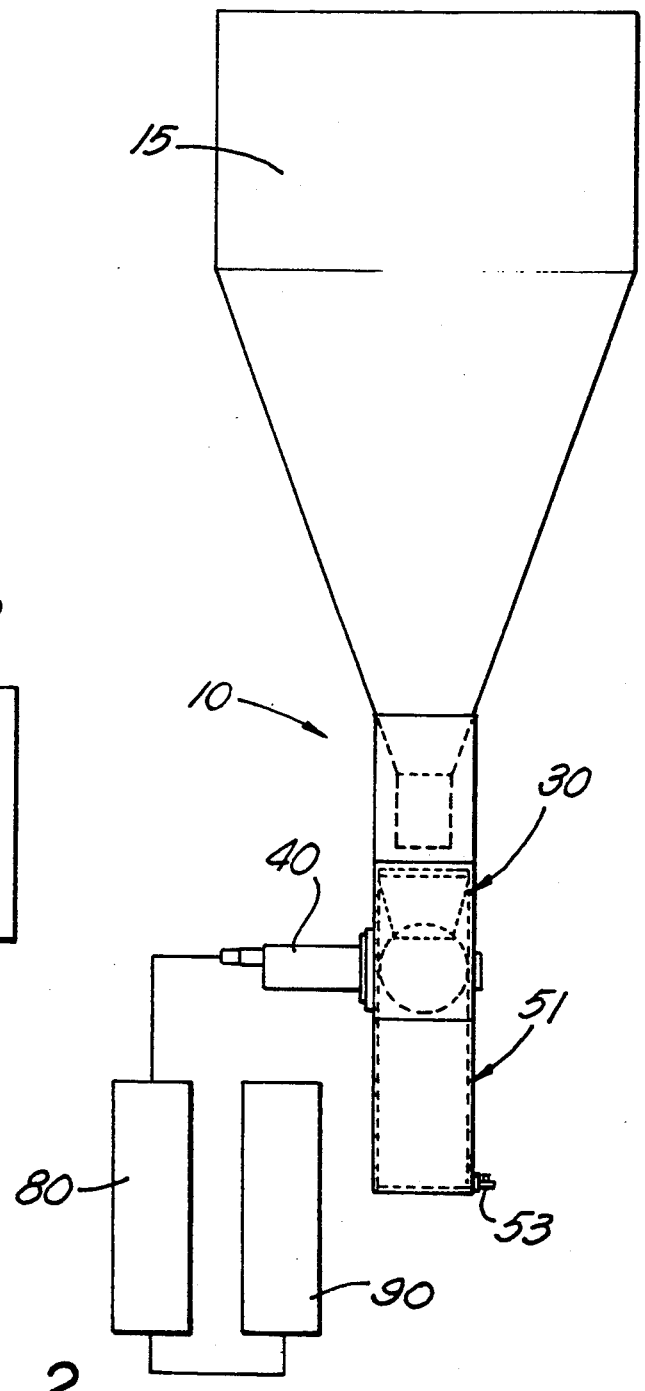
FIG. 2 is a schematic representation of a single sample, modular sediment trap of the present invention incorporating a wide-mouthed, conical interceptor.
Figure 4A:
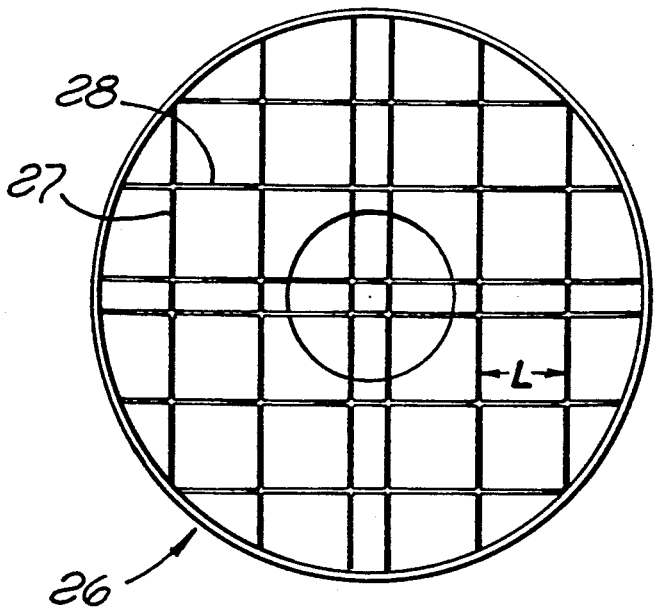
FIG. 4A shows the top, baffled portion of the funnel-shaped interceptor rotated by 90° to illustrate its configuration.

Sediment trap 10, illustrated in assembled form in FIGS. 1 and 2, provides accurate collection of the vertical particle flux in aquatic environments such as marine and lacustrine environments. The sediment traps described herein may also be employed in other liquid environments, such as industrial environments, to collect and measure the vertical particle flux. Apparatus and methods disclosed herein are useful, for example, for analysis in sewage treatment facilities or outfalls.

As shown in FIG. 1, preferred embodiments of sediment trap 10 include a particle interceptor chamber 20; a valve assembly 30; a sediment accumulator chamber 50; and a sediment collection assembly 60. Sediment collection assembly 60 provides multiple sampling capability. Drive means 40 and 70 operate valve assembly 30 and collection assembly 60, respectively. Control unit 80, such as a microprocessor, controls certain aspects of the valve and collection assemblies through their respective drive means. A power source 90 supplies power for drive means 40, 70 and control unit 80. Although sediment traps of the type shown in FIG. 1 are preferred for many aquatic applications, it will be recognized that simplified arrangements that exclude or combine one or more of the modular components may also be suitable for many applications.

FIG. 2 illustrates another preferred sediment trap suitable for single test sample applications. Tapered particle interceptor chamber 15 is mounted adjacent to valve assembly 30, and a single sediment collection chamber 51 is provided. Valve assembly 30 is operated by drive means 40, and microprocessor 80 controls operation of valve assembly 30 through drive means 40.

Each of the sediment trap components is preferably in modular form so that different components can be combined or exchanged to provide a variety of collection objectives and conditions. Thus, for example, different designs of particle interceptor chambers and collection assemblies may be interchanged at a supply source or in the field to provide enhanced versatility and collection effectiveness. Various modular components of the present invention may also be adopted for use with alternative trap designs. Moreover, a plurality of sediment traps may be linked to a common controller.

Figure 3A:
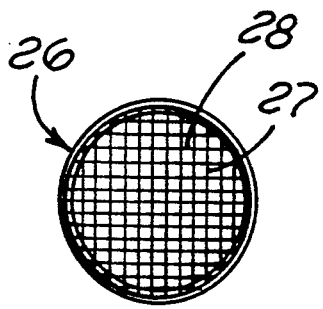
FIG. 3A shows the top, baffled portion of the particle interceptor chamber of FIG. 3 rotated by 90° to illustrate the configuration of the baffle.
Figure 3:
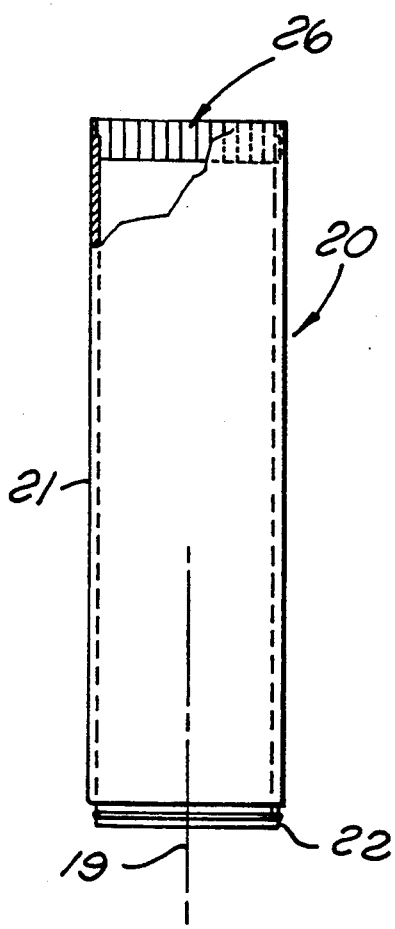
FIG. 3 is a side view of a cylindrical particle interceptor chamber for use in sediment traps.
Figure 4:
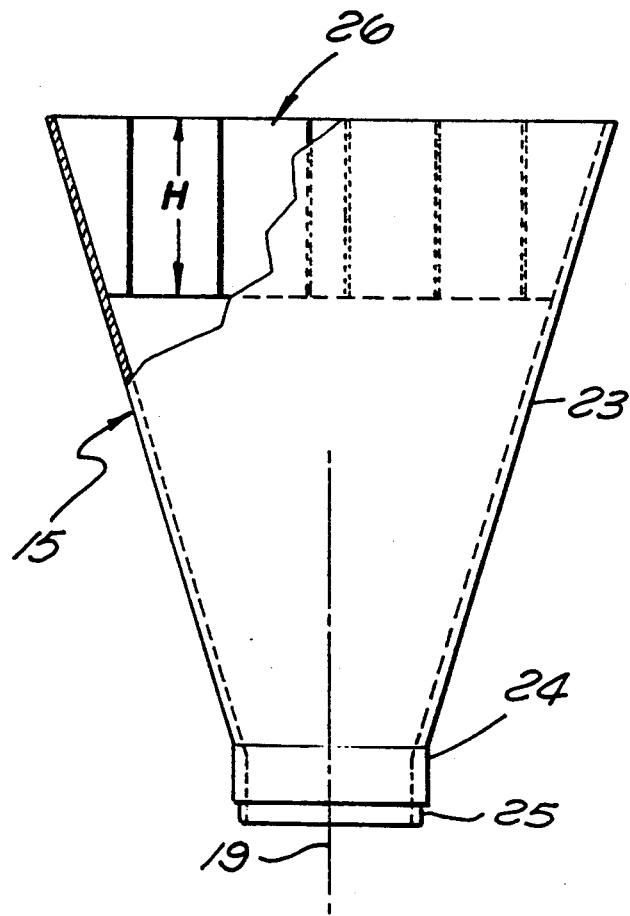
FIG. 4 shows a side view of a funnel-shaped particle interceptor chamber for use in sediment traps according to the present invention.

FIGS. 3 and 4 show two different embodiments of particle interceptor chambers having generally cylindrical and funnel-shaped configurations, respectively. As shown in FIG. 3, particle interceptor chamber 20 comprises a generally cylindrical tube 21 having attachment means 22 at its lower portion for attachment of particle interceptor chamber 20 to a valve assembly. Attachment means 22 preferably includes an annular recessed collar having a diameter slightly less than that of cylindrical tube 21. A groove in the recessed collar positions an O-ring, and attachment means 22 can therefore be friction fit with another modular component. Set screws or other fasteners may additionally be used to join the components.

Alternatively, as shown in FIGS. 2 and 4, the particle interceptor chamber may comprise a generally funnel-shaped portion 23 terminating, at its lower end, in cylindrical section 24 having attachment means 25 for attachment to a suitable valve assembly. As shown in FIG. 2, funnel-shaped particle interceptor chambers may additionally have an enlarged cylindrical section at their upper end. This embodiment facilitates insertion of baffles, or the like, at the entrance to the particle interceptor chamber. Funnel-shaped particle interceptor chambers permit collection of a higher volume of particulate material, but they are generally more prone to be influenced by hydrodynamic biases than are cylindrical particle interceptor chambers.

Regardless of its configuration, the particle interceptor chamber is preferably symmetrical with respect to the central longitudinal axis 19 of the sediment trap and preferably has a height:diameter ratio of at least about 2:1, and most preferably from about 3:1 to about 6:1. The inner surfaces of the particle interceptor chamber are smooth and non-porous to minimize adherence of particles to the chamber side walls. For many applications, it is preferred that the particle interceptor be constructed from a transparent or semi transparent material to provide monitoring capabilities. Suitable materials, including polymeric materials, fiberglass, and the like, are well known. Cast acrylic is an especially preferred material.

Baffle 26 may be provided in proximity to the upper portion of the particle interceptor chamber. Baffles are preferably provided as modular, removable components so that baffles having various configurations may be interchanged to suit various collection conditions. Baffles diminish turbulence within the interceptor chamber during sediment collection and, in particular, reduce eddy penetration as horizontal currents flow across the top of the sediment trap. Additionally, baffles prevent large organisms from entering the chamber.

Baffle 26, as illustrated in FIGS. 3 and 4, generally comprises a first series of partitions 27 oriented parallel to one another, and a second series of partitions 28 oriented parallel to one another and generally perpendicular to the first series of partitions. The baffle thus forms a grid-like assembly. The partitions are preferably relatively thin, flat slats arranged on a plane generally parallel to central longitudinal axis 19 of the sediment trap. Partitions 27 and 28 are preferably regularly spaced and provide a height (H):length (L) aspect ratio of at least about 1:1, and more preferably about 3:1. The vertical height of the baffle, shown as H in FIG. 4, is preferably from about 1% to about 25% of the total vertical height of the particle interceptor chamber.

Valve assembly 30 is interposed between particle interceptor 20 and the accumulator and/or collection chamber. Particles enter and sink toward the lower portion of the particle interceptor chamber and are intermittently transferred, by means of the valve assembly, to the chamber positioned adjacent and below the valve assembly. The valve assembly serves two principal functions: (1) it excludes live organisms from the accumulator portion of the trap; and (2) it isolates collected material from the particle interceptor chamber, thereby preventing washout and particle reprocessing by live organisms.

Figure 5A:
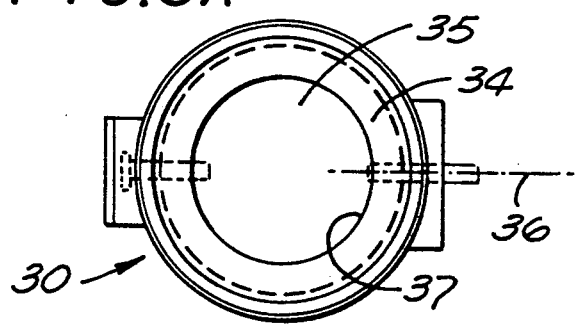
FIG. 5A shows a top view of the valve assembly of FIG. 5.
Figure 5:
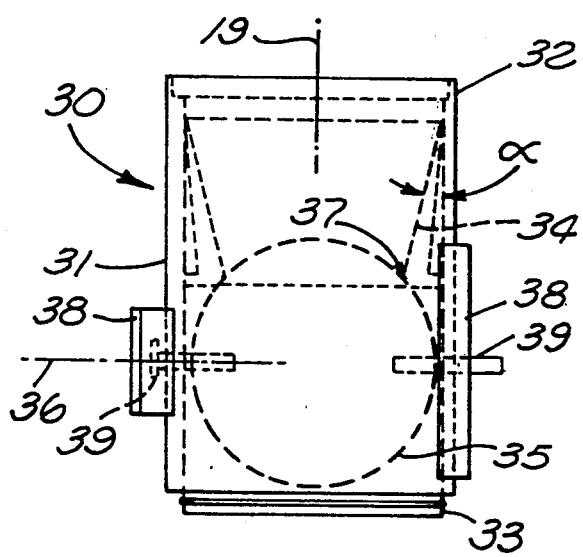
FIG. 5 is a schematic representation of a valve assembly suitable for use in sediment traps of present invention.

As shown in FIG. 5, valve assembly 30 comprises a cylindrical outer wall 31 enclosing tapered collar 34 and valve body 35. Valve assembly 30 also has attachment means 32 and 33 for attachment to particle interceptor and particle accumulator and/or collection chambers, respectively. Valve assembly 30 preferably isolates the particle interceptor and the accumulator and/or collection units from one another, except during transfer of sediment from the upper to the lower chamber.

Tapered collar 34 is preferably mounted in an upper portion of valve assembly 30 or a lower portion of the particle interceptor chamber so that a lower edge of collar 34 seals against valve body 35. The seal may be maintained, for example, by spring biasing the lower edge of collar 34 toward valve body 35. According to an especially preferred embodiment, a plurality of titanium springs are mounted in compressed form within notches in the outer collar surface to bias the lower edge of collar 34 against the surface of the valve body. Collar 34 thus provides a seal between spherical valve body 35 and the inner particle interceptor chamber wall and assists in isolating the upper particle interceptor chamber from the lower accumulator or collection chamber(s). As shown in FIG. 5, collar 34 is preferably tapered from the inner surface of cylindrical wall 31 toward central longitudinal axis 19 at an angle $\alpha$ of about 5° to about 50°. The contact interface 37 between collar 34 and a spherical valve body 35 is thus generally circular, with a circumference less than that of cylindrical wall 31.

Figure 6A:
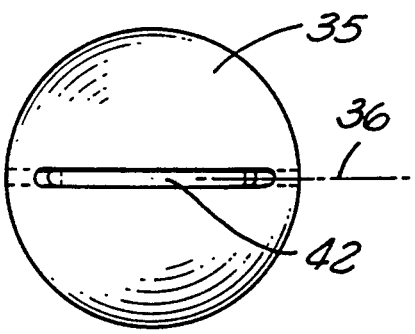
FIGS. 6A, 6B and 6C illustrate top, side and end views, respectively, of one embodiment of an indented valve body forming part of the valve assembly according to the present invention.
Figure 6B:
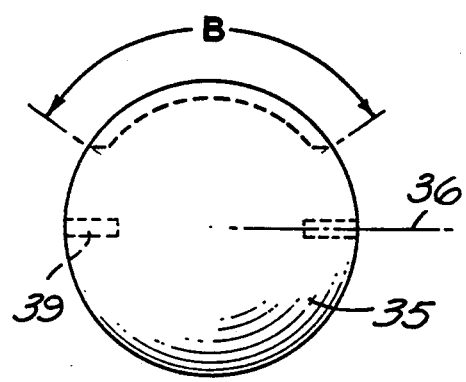
Figure 7:
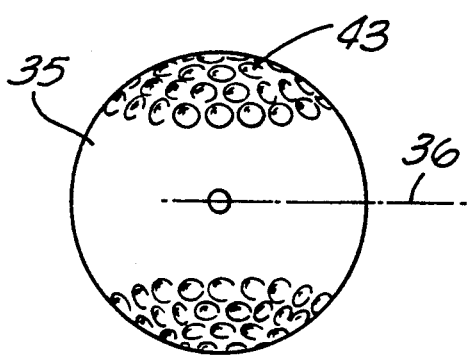
FIG. 7 illustrates another embodiment of an indented valve body in accordance with the present invention.
Figure 6C:
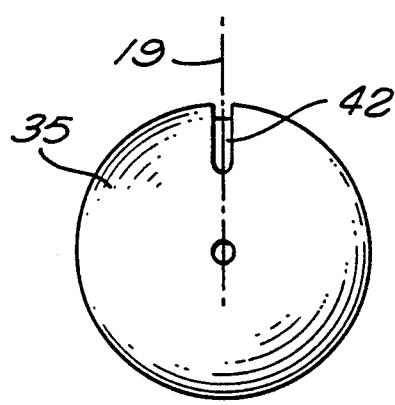

A preferred embodiment of indented valve body 35 is illustrated in FIGS. 6A–6C. FIG. 6A shows a top view of indented valve body 35, while FIG. 6B shows a side view of valve body 35 rotated 90° about transverse axis 36 from the view shown in FIG. 6A, and FIG. 6C shows an end view of valve body 35 rotated 90° about central longitudinal axis 19 from the view shown in FIG. 6B. FIG. 7 illustrates a preferred valve body having a plurality of indentations.

Valve body 35 preferably has a generally spherical or elliptical surface, and is symmetrical about both central longitudinal axis 19 and transverse axis 36. In the embodiment shown in FIG. 6, valve body 35 is spherical and has at least one indentation formed in the surface thereof. Sediment collection groove 42 is formed in a generally semi-hemispherical configuration. Sediment collection groove 42 preferably extends for up to about 50% of the circumference of valve body 35. Groove 42 and collar 34 are configured and positioned so that the length of groove 42 coincides generally with contact interface 37 between tapered collar 34 and valve body 35.

FIG. 6B illustrates a preferred embodiment wherein sediment collection groove 42 is formed in the spherical surface of valve body 35 symmetrically with respect to central longitudinal axis 19 along an arc B of about 70° to about 130°, and most preferably about 100°. An opposed groove having generally the same configuration and dimensions may also be provided. Sediment collection grooves preferably have bevelled side walls terminating in a curved or V-shaped channel.

Valve bodies having opposed groves or other bisymmetric indentation patterns are preferred for many applications, since they require only 180° rotation per transfer operation. A series of grooves or indentations may be provided in valve body 35 in place of or in addition to the continuous groove shown in FIG. 6, depending upon the desired particle transfer characteristics. The grooves or depressions are deep enough to accommodate the largest size particles being collected. Valve body 35 and tapered collar 34 may be constructed from polyvinyl chloride (PVC) or a variety of other materials, depending upon the nature of the particles being transferred and the application. The desired pattern of grooves or depressions may simply be machined into the surface of the valve body.

Various indentation configurations and patterns are suitable for collecting and/or transferring different particles under different operating conditions. One of the preferred embodiments for aquatic applications is illustrated schematically in FIG. 7. Valve body 35, as shown in FIG. 7, may have a golf ball-type design, in which approximately 55 adjacent semi-hemispherical indentations 43 approximately ⅜" in diameter and 0.12 inches deep are provided on two opposed surfaces of the valve body. The indentation pattern is preferably generally coextensive with the surface area of the valve body forming the bottom of the interceptor chamber during a collection operation. Other indentation patterns may also be used.

Indented, rotating valve body 35 is mounted within outer wall 31 of valve assembly 30 for rotation about transverse axis 36. Transverse axis 36 is aligned coincident with the midline of valve body 35 and perpendicular to central longitudinal axis 19 of the sediment trap. As shown in FIG. 5, mounting means 39 may be provided in valve body 35 aligned with transverse axis 36. Interchangeability of valve bodies 35 within valve assembly 30 is a desirable feature, since different valve body configurations may be preferred for various applications. Valve body 35 is preferably rotatably mounted on drive shafts 39 operably connected to drive means 40. Enlarged mounting means 38 are preferably provided to support drive shafts 39 and valve body 35. Drive means 40 is preferably controlled by programmable microprocessor unit 80. In this fashion, the frequency and rate of valve body rotation can be adapted for various sediment collection environments and sampling objectives.

In a particle interception, non-transfer position, rotating valve body 35 is stationary. In single groove valve body embodiments of the type shown in FIGS. 6A–C, the groove faces the lower accumulator unit during particle interception and is rotated one full revolution during a particle transfer cycle. In bisymmetrically valved traps employing a valve body of the type illustrated in FIG. 7, an indented portion of the valve body forms the floor of the interceptor chamber during collection, and the valve body is rotated one half revolution during a particle transfer cycle.

As sediment particles enter particle interceptor chamber 20, they migrate toward the bottom of the chamber and collect on the exposed surface of valve body 35, which effectively forms a bottom wall of the accumulator chamber. As a result of the curved configuration of valve body 35, sediment particles collect particularly at the interface of valve body 35 with tapered collar 34. At predetermined time intervals, valve body 35 is rotated a full or partial revolution in a particle transfer cycle. As the valve body rotates, particles collected at the interface of collar 34 with valve body 35 fall into the groove(s) or indentation(s) provided in the valve body and are transferred beneath the sealing collar and into the adjacent particle accumulator and/or collection unit. The valve body rotation required to effect particle transfer depends upon the type and pattern of indentations provided on the valve body. In general, for example, bisymmetric indentation patterns require valve rotations of 180° per particle transfer cycle. Particularly in environments where power is a limiting resource, transfer cycles requiring 180° valve body rotations or less are desirable.

Utilization of a valve assembly comprising a rotating, indented valve body substantially reduces sampling error resulting from the presence of swimmers in sediment collection samples. Only if living organisms become entrapped in the sediment collection groove(s) during rotation of the valve body are they transferred to the accumulator chamber. Moreover, utilization of this type of valve assembly reduces sampling error resulting from grazing, particularly if the valve body is rotated at relatively high frequencies. High frequency rotation, in this context, is generally once or twice each hour, or more. The sediment collected in the particle interceptor chamber is only available for grazing by living organisms during the time periods between valve body rotations and is isolated from living organisms in the particle interceptor chamber after it has been transferred. Interchangeability of modular valve assemblies and/or valve bodies within valve assemblies is also an important feature, since it permits adaptation of the collection and transfer mechanism to the size, density and adhesiveness of particles being collected. The rotating, indented valve body thus provides many advantages and is an important feature of sediment traps of the present invention.

The particle accumulator unit positioned adjacent and below valve assembly 30 is another generally cylindrical chamber that may serve as a collection chamber, as shown in FIGS. 2 and 8, or as a particle focusing means, as shown in FIGS. 1 and 9. In either case, the particle accumulator chamber comprises a cylindrical chamber having a height:diameter ratio of at least about 1:1 and preferably from about 2:1 to about 6:1.

As shown in FIG. 8, the particle accumulator chamber may simply comprise a cylindrical chamber 51 having attachment means 52 for sealing with valve assembly 30 and defining a single, relatively large collection chamber. Valve 53 penetrates cylindrical chamber 51 near its bottom wall to provide access to the lower collection portion of the chamber and to permit introduction of solutions containing, for example, poison or preservative compositions. When the accumulator chamber is utilized as a collection chamber as illustrated in FIG. 2, a preservative material is preferably suspended in a dense brine solution in the collection zone near the bottom of the accumulator chamber. The brine solution prevents the preservative and/or poison material from migrating throughout the accumulator chamber.

Alternatively, as shown in FIGS. 1 and 9, the particle accumulator chamber may comprise cylindrical chamber 55 having attachment means 56 and 57 at the top and bottom, respectively, for attachment to valve and sediment collection assemblies, respectively. Additionally, the accumulator chamber is preferably provided with skewed funnel 58 terminating in sediment outlet 59 at the bottom and near the perimeter of cylindrical chamber 55. Focussing funnel 58 is skewed to one side of cylindrical chamber 55 to direct the collected particles into sediment outlet 59. Valve body 35 and focussing funnel 58 are preferably arranged and operate so that particles transferred to the accumulator chamber by valve body 35 are deposited on the most steeply angled portion of the focussing funnel.

In embodiments wherein the accumulator chamber serves a particle focussing rather than a collection function, collection assembly 60 is preferably mounted immediately below or within a lower portion of the accumulator chamber. As shown in FIG. 10, collection assembly 60 is preferably an independent modular unit comprising outer cylindrical section 61 having attachment means 62 near its upper edge for attachment to the accumulator chamber, and bottom wall 63. A multiple sample rosette 64 that supports a plurality of collection vials 66 is mounted within cylindrical section 61. Collection vials 66 are preferably positionable in a radial arrangement in proximity to cylindrical section 61. Rosette 64 is preferably removable from collection assembly 60 to facilitate interchange of rosettes having different configurations and accommodating collection vials having a variety of configurations and dimensions. Upon rotation of sediment collection vials 66 mounted in rosette 64 about central longitudinal axis 19, different collection vials are positioned beneath sediment outlet 59 to collect sediment samples, thus providing collection of temporally resolved sediment samples over predetermined time intervals.

According to preferred embodiments, collection vials 66 are spring-biased toward the accumulator chamber. The openings of the collection vials are preferably sealed by compression against the lower wall of the accumulator unit, except when a collection vial is aligned with sediment outlet 59. The volumetric capacity of the collection vials may vary, and is generally larger for longer sample collection and deployment periods. The length of collection vials must, however, be sufficient to prevent preservatives and dissolved constituents from diffusing out of the vial during the collection period. The length-to-diameter ratio of collection vials 66 is preferably at least 3:1. Suitable collection vials include glass centrifuge tubes, and the like.

As shown schematically in FIG. 1, collection assembly 60 is mounted on a drive shaft operably connected to drive means 70, which is controlled by control unit 80, such as a programmable microprocessor. In this fashion, collection vials can be rotated at time intervals ranging from hours to months, and time intervals between rotations may be varied as desired. Additionally, valve assembly 30 is operated by drive means 40 controlled by control unit 80. Power source 90 provides operating power to both the drive means and the control unit, if necessary. The drive means, control unit and power source are sealed in a liquid-tight pressure compensating casing that protects them from aquatic environments and the effects of elevated pressure conditions.

Many types of commercially available drive units and programmable microprocessor units are suitable for use in the present invention. DC motors and corresponding gearheads known as MicroMo, available from MicroMo Electronics, Inc., are especially preferred for operating valve assembly 30 and collection assembly 60. Motor housings are preferably constructed from cast acrylic and filled with Fluorinert FC-77 ® (3M Company), thereby allowing visual inspection of operation and detection of corrosion or electrolysis. A double "O" ring seal, self-flushing motor mount is used on the valve assembly module to prevent contamination of the traps by the Fluorinert ®.

Drive motors for driving the valve and collection assemblies are preferably precisely positioned by means of an optical sensor and a slotted disk attached to the motor shaft(s). The disk for the ball valve has a single slot for full rotation transfer cycles and two slots 180° apart for one half rotation transfer cycles. The slotted disk for controlling rotation of the collection rosette and vials has a number of equally spaced slots corresponding to the number of collection vials. The state of the optical sensor is monitored by the control unit, which in turn starts and stops the motor.

Tattletale IV ® microprocessor units, available from ONSET Computer Corp., are especially suitable for sediment trap applications. The microprocessor unit is also enclosed in liquid-tight pressure casing. Programming of and communication with a Tattletale ® microprocessor unit may be achieved using an RS-232 serial link to a standard personal computer. The microprocessor can be controlled using a modified BASIC language.

A single Tattletale ® microprocessor unit is capable of controlling up to eight motor drives and thus can operate up to four sediment traps of the type illustrated in FIG. 1, employing both motor driven valve and sediment collection assemblies. Control of additional features can also be provided by the microprocessor unit, such as coordination of the valve and collection assemblies with underwater visual monitoring devices, such as underwater VCR. Storage of diagnostic data in the microprocessor unit may also be provided. Power for operating two DC motors and a Tattletale microprocessor unit for deployment periods of up to one year may be provided by eight (8) lithium size DD cells.

Attachment means for joining various components of the sediment trap seal the components to prevent contamination. Provision of liquid-tight seals between cylindrical components having substantially the same diameter is well-known, and various sealing means may be employed. According to preferred embodiments, modules are mounted and held together using O-rings and stainless steel set screws.

Particle interceptor, accumulator and collection chambers are preferably constructed from rigid or semirigid materials that are impermeable to particulate materials and noncorrosive in aquatic, and particularly marine environments. The interior chamber walls are preferably resistant to particle collection and adhesion and growth of aquatic organisms. Modular sediment trap components are preferably designed and assembled to provide smooth, flat interior surfaces. Substantially transparent polymeric materials such as polycarbonate, acrylic, fiberglass, and the like are especially preferred, since they permit in situ monitoring during particle collection.

Sediment traps according to the present invention were field tested to determine whether they in fact minimized collection of animate organic material or distortion resulting from the presence of swimmers, sample reprocessing, and particle washout. The specific valved sediment traps used in this study were of the "Indented Rotating Sphere" (IRS) type. These traps were of cylindrical design (e.g., FIG. 1) and equipped with a 6 inch diameter, 3:1 aspect ratio interceptor module fit with standard baffles (FIG. 3). A simple particle collector (e.g. FIG. 9) was used in all deployments. All traps were fitted with spherical valve body having a single groove (FIG. 6A-C) that rotated 360° during each particle transfer circle. Rotation frequencies of the valve assemblies on ARS traps were either once per hour or once per half hour. The IRS assemblies were compared to a variety of other sediment traps, including simple 3:1 Lorenzen-type cylinders, PIT-type collectors often used for open ocean applications, and no-valve control (NVC) traps which are identical to the IRS trap except for the spherical valve.

The site chosen for initial field testing of the IRS traps was a temperate, fjord-like embayment, Dabob Bay, Wash., which has been the location of numerous oceanographic investigations over the past 25 years. Dabob Bay mimics biological cycles in the open temperate ocean with annual spring and fall blooms and planktonic assemblages closely resembling those typically found in productive marine environments.

A total of six deployments of IRS-type sediment traps were made. Traps were deployed in octagonal holders at 50 m depth on bottom-tethered, moorings in 110–120 m of water. During the first set of deployments, two valved IRS and two no-valve control (NVC) traps were placed on a single octagonal array 90° apart. During a second set of deployments, duplicate octagons were fully loaded with the additional Lorenzen—and PIT-type trap in order to directly compare the amounts and compositions of swimmers and passively sinking particles collected by traps having different designs.

Before deployment, all traps were filled with filtered (5 mm pore size) seawater. Treatments used were brine only, salt plus 500 mg $HgCl_2$/L or salt plus 20 ml/L formalin; untreated traps contained filtered seawater only. Total traps samples were first wet sieved through 850 $\mu$m sieve, which isolated primarily large zooplankton carcasses. Samples selected for multiple chemical analysis were split into fractions for separate analyses of total mass, organic carbon (OC), total nitrogen (TN), lipid, pigment and amino acid. Lipid, pigment and amino acid analyses were performed only on samples from IRS and NVC traps, which are the primary focus of the following analysis.

The chemistry of the vertical particle flux in Dabob Bay is markedly affected by live zooplankton entering the traps and subsequently being killed by the various chemical treatments used to prevent microbial degradation. The evidence for swimmer artifacts is summarized in the following findings comparing samples collected from various trap types.

In treated traps >850 $\mu$m mass fluxes range from 7 to 38% of the total mass flux in open NVC taps, but never exceeded 7% in IRS valved traps. The >850 $\mu$m mass flux for unpoisoned traps was equivalent to the average >850 $\mu$m mass trapped in all IRS valve traps, indicating the IRS valve was extremely effective at excluding large swimmers. Furthermore, >850 $\mu$m mass fluxes were 10–15% lower in IRS traps than in corresponding NVC traps, suggesting that IRS traps excluded material >850 $\mu$m as well.

OC and TN concentrations were significantly lower in IRS traps relative to NVC traps, indicating that the material excluded is organic matter. OC/TN ratios are higher for material caught in IRS traps relative to NVC traps, consistent with the exclusion of marine derived organic matter. For paired, treated traps, the ratio of amino acid concentrations in the IRS traps versus the NVC controls averaged 0.76±0.26 and amino acid fluxes averaged 0.53±0.15, while untreated IRS and NVC traps were statistically indistinguishable. Amino acids are marine derived, suggesting that marine derived organic matter is being excluded from the IRS traps. Moreover, the concentrations and fluxes of lipid compounds from classes specific to animals are more reduced in IRS traps than amino acids which trace both plants and animals. This indicates that the excluded marine derived organic matter has a significant zooplankton component.

The experimental results demonstrated that the material caught in biocide-treated IRS traps is substantially different from that collected in open counterparts, as determined by both gravimetric and chemical analyses. Moreover, as the measured parameter becomes a more specific indicator for zooplankton material, the extent of depletion of that material in the valved sediment trap becomes greater compared to the valve-free control. In addition, washout of biocide or sample from an IRS trap was not observed during any field study. Both laboratory and field studies support the conclusion that the rotating valve efficiently transfers natural particles from the interceptor to the collector module. The experimental results demonstrate that the IRS trap does, in fact, accomplish its objectives of minimizing zooplankton reprocessing and the collection of swimmers, while avoiding washout of both sample and biocide.

It will be obvious to those having skill in the art that many changes may be made to the details of the above-described preferred embodiments of the present invention without departing from the underlying principles thereof. The configuration of the modules need not be cylindrical, for example, and additional modules providing additional sampling and/or testing functionalities may be provided. The scope of the present invention is, therefore, determined only by the following claims.

We claim:
1. An apparatus for collecting particles comprising:
   a first particle interceptor chamber having a substantially continuous side wall;
   a second particle collection chamber having a substantially continuous side wall and a sealable particle outlet;
   a valve assembly interposed between the first and second chambers capable of providing a seal between the first and second chambers and transferring particles from the first to the second chamber during a particle transfer operation;
   a plurality of discrete sediment collection vials positioned in proximity to the second chamber for receiving particles collected at the particle outlet; and
   means for sequentially positioning discrete sediment collection vials adjacent the particle outlet at different times to provide a plurality of temporally resolved particle samples.

2. An apparatus in accordance in claim 1, wherein the valve assembly comprises a rotatable, indented valve body.

3. An apparatus in accordance with claim 2, wherein the valve body is generally spherical or elliptical.

4. An apparatus in accordance with claim 2, wherein the valve body has a groove formed in its exterior surface extending for up to about 50% of its circumference.

5. An apparatus in accordance with claim 2, wherein the valve body has at least two indentations forming a symmetrical indentation pattern.

6. An apparatus in accordance with claim 2, wherein the valve assembly additionally comprises a tapered collar positioned so that one edge of the tapered collar is capable of forming a seal with the valve body.

7. An apparatus in accordance with claim 6, wherein the valve body has a groove formed in its exterior surface and the groove and tapered collar are configured and positioned so that the groove coincides generally with the interface between the tapered collar and the valve body upon rotation in the valve body.

8. An apparatus in accordance with claim 1, wherein the side wall of the first chamber has a tapered configuration.

9. An apparatus in accordance with claim 1, wherein the means for sequentially positioning discrete sediment collection vials is a motor drive, and the motor drive is controlled by a microprocessor unit.

10. An apparatus in accordance with claim 9, wherein the motor drive is positioned by means of an optical sensor and the state of the optical sensor is monitored by the microprocessor unit.

11. An apparatus in accordance with claim 1, wherein the second chamber includes an internal focussing funnel terminating at the particle outlet.

12. An apparatus in accordance with claim 1, wherein the discrete sediment collection vials are arranged in a radial configuration.

13. An apparatus in accordance with claim 12, wherein the first and second chambers and the valve assembly are arranged generally symmetrically about a central longitudinal axis, and the particle outlet and the sediment collection vials are rotatable with respect to one another about the central longitudinal axis to sequentially locate different particle collection vials in a collection position adjacent the particle outlet.

14. An apparatus in accordance with claim 1, wherein the first chamber, the second chamber and the valve assembly comprise modular components that are readily attachable to and detachable from one another.

15. An apparatus in accordance with claim 1, wherein the sediment collection vials have openings that are biased toward the second particle collection chamber and sealed against a wall of the second chamber.

16. An apparatus for collecting particulate samples comprising:
   a first particle interception chamber having a central longitudinal axis;
   a second particle accumulator chamber aligned on the central longitudinal axis and having a sealable particle outlet;
   a valve assembly interposed between and capable of providing a seal between the particle interception and accumulator chambers, the valve assembly comprising an indented valve body rotatable about a rotational axis transverse to the central longitudinal axis to selectively transfer particles from the first particle interception chamber to the second particle accumulator chamber;
   a sediment collection vial positioned in proximity to the particle outlet and having an opening communicating with the particle outlet; and
   a tapered wall extending between the valve assembly and the particle outlet to direct particles from the second particle accumulator chamber to the opening of the sediment collection vial.

17. An apparatus in accordance with claim 16, wherein the valve body has a groove formed in its exterior surface extending for up to about 50% of its circumference.

18. An apparatus in accordance with claim 16, wherein the valve body has at least two indentations forming a symmetrical indentation pattern.

19. An apparatus in accordance with claim 16, wherein the valve assembly additionally comprises a tapered collar positioned so that one edge of the tapered collar is capable of forming a seal with the valve body.

20. An apparatus in accordance with claim 16, wherein the side wall of the first chamber has a tapered configuration.

21. An apparatus in accordance with claim 16, comprising a plurality of sediment collection vials mounted radially on a rotatable carousel and additionally comprising means for rotating the carousel to sequentially locate predetermined sediment collection vials at the particle outlet.

22. An apparatus in accordance with claim 21, wherein the means for rotating the carousel is a motor drive, and the motor drive is controlled by a microprocessor unit.

23. An apparatus in accordance with claim 22, wherein the motor drive is positioned by means of an optical sensor and the state of the optical sensor is monitored by the microprocessor unit.

24. An apparatus for collecting particulate samples comprising:

an first particle interception chamber having substantially continuous side walls and a central longitudinal axis;

a second particle accumulator chamber having substantially continuous side walls and aligned on the central longitudinal axis;

a valve assembly interposed between and capable of providing a seal between the particle interception and accumulator chambers, the valve assembly comprising an indented valve body rotatable about a rotational axis transverse to the central longitudinal axis, the indented valve body having at least two indentations provided in a symmetrical indentation pattern.

25. An apparatus according to claim 24, wherein the indented valve body has two indentations and the indentation pattern is bisymmetrical.

26. An apparatus according to claim 24, wherein the second particle accumulator chamber has a sealable particle outlet, and additionally comprising a plurality of discrete sediment collection vials positioned in proximity to the second chamber for receiving particles collected at the particle outlet and means for sequentially positioning discrete sediment collection vials adjacent the particle outlet means at different times, thereby providing a plurality of temporally resolved particle samples.

* * * * *